United States Patent [19]

Hirota et al.

[11] Patent Number: 4,960,595
[45] Date of Patent: Oct. 2, 1990

[54] LIPID MEMBRANE STRUCTURES

[75] Inventors: Sadao Hirota; Hiroshi Kikuchi; Hitoshi Yamauchi; Munehiro Tomikawa, all of Tokyo, Japan

[73] Assignee: Daiichi Seiyaku Co., Ltd., Tokyo, Japan

[21] Appl. No.: 222,309

[22] Filed: Nov. 16, 1987

Related U.S. Application Data

[63] Continuation of Ser. No. 795,608, Nov. 6, 1984, abandoned.

[30] Foreign Application Priority Data

Nov. 6, 1984 [JP] Japan ................. 59-233742

[51] Int. Cl.$^5$ .................. A61K 37/22; A61J 5/04; B32B 3/26
[52] U.S. Cl. ................... 424/450; 264/4.1; 428/321.5
[58] Field of Search ............ 424/417, 450; 264/4.1, 264/4.3, 4.6; 428/402.2

[56] References Cited

U.S. PATENT DOCUMENTS 4,323,561 4/1982 Nowotny ............... 536/18
4,377,567 3/1983 Geho ..................... 424/85
4,416,872 11/1983 Alving et al. .......... 260/112.5 R
4,485,045 11/1984 Regen .................... 424/38

FOREIGN PATENT DOCUMENTS 0094692 11/1983 European Pat. Off. .
1080265 4/1960 Fed. Rep. of Germany ........ 424/38
8304412 12/1983 PCT Int'l Appl. .
2134869 8/1984 United Kingdom .

OTHER PUBLICATIONS

"Routes to Functional Vescile Membrane without Proteins", Fuhrop et al. in 2260 Angewandte Chemie, pp. 100–113.
Chemical Abstracts, vol. 85, Abstract No. 188420u, "Condensation of D–Glycosylamines, etc.," Mocczar et al.
Chemical Abstracts, Ninth Collective Index, vols. 76–85, p. 2707CS.

Primary Examiner—Douglas W. Robinson
Assistant Examiner—Raymond J. Henley, III
Attorney, Agent, or Firm—Sughrue, Mion, Zinn, Macpeak & Seas

[57] ABSTRACT

Lipid membrane structures containing a lactose monofatty acid ester or amide are disclosed. The lipid membrane structures are delivered preferentially to the liver parenchymal cells and are useful as carriers of drugs.

3 Claims, No Drawings

LIPID MEMBRANE STRUCTURES

This is a Continuation of application Ser. No. 795,608 filed Nov. 6, 1984, now abandoned.

FIELD OF THE INVENTION

This invention relates to lipid membrane structures and, more particularly, to lipid membrane structures containing a lactose monofatty acid ester or a lactose monofatty acid amide (hereinafter abbreviated as lactose monofatty acid ester or amide) in the lipid membrane thereof. The lipid membrane structures of this invention are delivered preferentially to the liver parenchymal cells and are useful as carriers of drugs in medical treatment.

BACKGROUND OF THE INVENTION

In an attempt to deliver drugs to the liver, various studies on liposome preparations have been conducted. Inter alia, the report by Surolia et al. in B.B.A., 497, 760–765 (1977), Japanese Patent Application (OPI) No. 98121/80 (the term "OPI" as used herein means "unexamined published patent application") and the report by Scherphof et al. in B.B.A., 734, 40–47 (1983) are known as studies on delivering of liposome preparations to the liver parenchymal cells.

In case of these prior art techniques, the liposomal lipid membrane contains naturally-occurring substances, such as asialoganglioside, digalactosyl diglyceride, lactosylceramide, etc., in order to deliver the liposomes to the liver parenchymal cells. It is difficult, however, to produce liposomes containing such naturally-occurring substances in the lipid membrane thereof on an industrial scale, though possible in laboratories, because of the difficulty in production of these naturally-occurring substances in a large quantity on an industrial scale.

SUMMARY OF THE INVENTION

The present inventors have conducted extensive and intensive investigations on lipid membrane structures which can be delivered or directed specifically to the liver parenchymal cells and can be produced in a large quantity on an industrial scale, and completed the present invention.

The present invention relates to lipid membrane structures containing a lactose monofatty acid ester or amide in the lipid membrane thereof.

DETAILED DESCRIPTION OF THE INVENTION

The lactose monofatty acid ester which can be used in the present invention is a compound wherein an acyl group having from 12 to 30 carbon atoms is bonded to one of the hydroxyl groups of the glucose moiety of lactose and can be prepared by the reaction of lactose and a fatty acid halide.

The lactose monofatty acid amide which can be used in the present invention is a novel compound wherein an acyl group having from 12 to 30 carbon atoms is bonded to one of the hydroxyl groups of a glucose moiety of lactose through an acid amide linkage. can be prepared as follows. That is, the hydroxyl groups of lactose are protected with suitable protecting groups such as benzyl group, benzilidne group, acetyl group, and an amino group is introduced to the desired site of the glucose moiety of the protected lactose using known methods. The amino-product is reacted with a fatty acid or its halide using known methods to give a lactose monofatty acid amide wherein the acylamino group is bonded to the desired site of the glucose moiety of lactose.

For example, 1N-acyl-1-deoxy-lactosyl amine can be prepared as follows. That is, lactose is reacted with acetic acid to protect the hydroxyl groups with acetyl groups and the product is reacted with a bromine compound such as hydrobromide to substitute the acyloxy group with bromine atom at the 1-position of glucose moiety. The product is reacted with an azide compound such as sodium azido and the product is catalytically reduced to give lactosylamine wherein the hydroxy groups are protected with acetyl groups. The product is reacted with a fatty acid and the protecting groups are removed by reacting the product with a sodium alkoxide to give the 1-N-acyl-1-deoxy-lactosyl amine.

The lactose monofatty acid ester and the lactose monofatty acid amide can be represented by the following chemical structure.

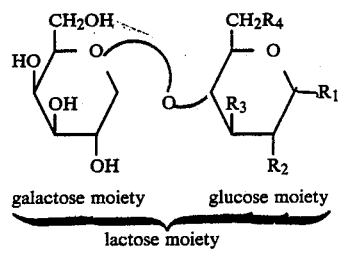

wherein one of $R_1$, $R_2$, $R_3$ and $R_4$ represents -O-acyl or -NH-acyl and the remaining three represent -OH.

As the representative compound of lactose monofatty acid or amine, 1-N-arachidyl (=eicosanoyl)-1-deoxy-lactosyl amine, 1-arachidyl lactose, 6-N-arachidylamino-6-deoxy-lactose and 6-arachidyl lactose can be shown.

The acyl group includes those derived from saturated or unsaturated fatty acids, such as a dodecanoyl group, a pentadecanoyl group, an octadecanoyl group, an eicosanoyl group, a hexacosanoyl group, a triacontanoyl group, a 4-dodecenoyl group, a 5-dodecenoyl group, a 9-hexadecenoyl group, a 9-octadecenoyl group, a 11octadecenoyl group, a 13-dococenoyl group, a 15-tetracosenoyl group, a 9,12-octadecadienoyl group, a 9,12,15octadecatrienoyl group, a 4,8,12,16-eicosatetraenoyl group, a 4,8,12,15,19-docosapentaenoyl group, etc.

In the preparation of lactose monofatty acid esters, a compound wherein a hydrogen atom of the 6-hydroxyl group of the galactopyranose moiety of lactose is substituted for an acyl group is sometimes by-produced, but the reaction product containing such a by-product may be used in the present invention.

The lipid membrane structures according to the present invention mean lipid particles wherein polar head groups are oriented towards an interface with an aqueous phase to form membrane structures and specifically include liposomes, water-soluble micelles, microemulsions, and the like.

Processes for preparing the lipid membrane structures of this invention are described below taking, for instances, the following lipid membrane structures.

(a) Preparation of Liposomes Containing Lactose Monofatty Acid Ester or Amide in the lipid membrane thereof:

An aqueous dispersion of liposomes is prepared using membrane components, such as phospholipids, e.g., lecithin, sphingomyelin, diacylphosphatidylethanolamine,, etc., glycolipids and dialky type synthetic amphiphiles in a known manner as described in *Annual Review of Biophysics and Bioengineering,* 9, 467–508 (1980). The above components may contain as auxiliary materials, as membrane stabilizers sterols such as cholesterol, cholestanol, etc., charged modifiers such as dialkyl phosphates, diacylphosphatidic acids, stearylamine, etc., and antioxidants such as α-tocopherol, etc. An aqueous solution or dispersion of a lactose monofatty acid ester or amide is added to the liposome suspension, and the mixture is allowed to stand for a given time, preferably under warming at a temperature above the phase transition temperature of the membrane or above 40° C., followed by cooling, to thereby prepare liposomes containing a lactose monofatty acid ester or amide in the lipid membrane thereof. Liposomes containing a lactose monofatty acid ester or amide in the lipid membrane thereof may also be prepared by previously mixing the aforesaid membrane components and the lactose monofatty acid ester or amide and treating the mixture according to a known process for preparing liposomes.

(b) Preparation of Micelles Containing Lactose Monofatty Acid Ester or Amide in the lipid membrane thereof:

Micelle-forming surface active substances, e.g., polyoxyethylene sorbitan fatty acid ester (Tween), sodium salt of fatty acid, bile salts, etc., are added to water at a concentration above the critical micelle concentration (CMC) to prepare micelles An aqueous solution or dispersion of a lactose monofatty acid ester or amide is then added to the micelle dispersion, and the mixture is allowed to stand for a given time, preferably under warming at a temperature above 40° C., followed by cooling, to prepare micelles containing a lactose monofatty acid ester or amide in the lipid membrane thereof. Alternatively, micelles containing a lactose monofatty acid ester or amide in the lipid membrane thereof may also be prepared by previously mixing the micelle-forming substances and the lactose monofatty acid ester or amide and treating the mixture in a known manner to prepare micelles/

(c) Preparation of Microemulsions Containing Lactose Monofatty Acid Ester or Amide in the lipid membrane thereof:

The micelles as prepared in (b) above are saturated with oils and fats, e.g., soybean oil, to increase an oil phase to such an extent that an irreversible oil layer separation does not occur, to thereby prepare microemulsions containing a lactose monofatty acid ester or amide in the lipid membrane thereof. Further, microemulsions containing a lactose monofatty acid ester or amide in the lipid membrane thereof can also be obtained by adding an aqueous solution or dispersion of a lactose monofatty acid ester or amide to microemulsions prepared in a known manner and allowing the mixture to stand for a given time, preferably under warming at a temperature above 40° C., followed by allowing to cool.

In the above-described preparation of lipid membrane structures, the kind of the resulting lipid membrane structures can be altered by varying the ratio of the lactose monofatty acid ester or amide to the total lipid components. For example, in the case of using lecithin as a sole lipid component other than the lactose monofatty acid ester or amide, liposomes are produced when the molar ratio of the lactose monofatty acid ester or amide to the total lipid components is adjusted to about ⅜ or smaller; and micelles or microemulsions are produced when the above-described ratio is greater than about ⅜.

In order to deliver the lipid membrane structures of the present invention to the liver parenchymal cells, it is usually desirable that the molar ratio of the lactose monofatty acid ester or amide to the total lipid membrane components is adjusted to about 1/40 or greater.

The drug which can be contained in the lipid membrane structures of the present invention varies depending on the kind of the lipid membrane structures. For example, drugs to be contained in the liposomes are not particularly restricted and include water soluble drugs and lipid soluble drugs. Drugs to be contained in the micelles include water insoluble drugs, and drugs to be contained in the microemulsions include oil soluble drugs.

In the lipid membrane structures according to this invention, the lactose monofatty acid ester or amide is incorporated tightly into the lipid membrane by hydrophobic interaction. It was confirmed by gel filtration that the suspension of lipid membrane structures contains only a very small amount of a lactose monofatty acid ester or amide as a free monomer.

The lipid membrane structures possess excellent delivery to the liver parenchymal cells and can be produced on an industrial scale with good reproducibility. Further, the lipid membrane structures that can be delivered to the liver parenchymal cells by the conventional techniques are limited only to liposomes, while the present invention can be applied not only to liposomes but also to micelles, microemulsions and the like. Furthermore, in the conventional techniques, substances delivering the lipid membrane structures to the liver parenchymal cells are water insoluble. To the contrary, most of the lactose monofatty acid ester or amide which can be used in the present invention are water soluble and, therefore, can easily be incorporated into lipid membrane structures by mixing an aqueous solution thereof with an aqueous dispersion of a commercially available lipid membrane structures and then incubating the mixture.

In particular, lactose monofatty acid amide with an acyl group is bonded to the 1-position of the glucose moiety of lactose through an acid amide linkage can easily be isolated and is especially preferred when used as a single component.

The present invention will now be illustrated in greater detail with reference to the following reference examples, examples and test examples, but it should be understood that the present invention is not limited thereto. In these examples, all the percents are given by weight unless otherwise indicated.

REFERENCE EXAMPLE 1

In 75 ml of water was dissolved 180 g of lactose, and a 50% sodium hydroxide aqueous solution was added thereto to adjust to a pH of 9. To the solution was slowly added 125 g of arachidyl chloride at 50° C. while maintaining at pH 9 with a 50% sodium hydroxide aqueous solution and maintaining moderate fluidity of the mixture by adding 125 g of water in small portions, followed by stirring at that temperature for an additional 1 hour. The precipitate was filtered and recrystallized from methanol. The resulting crystals were used as a lactose monoarachidic acid ester.

REFERENCE EXAMPLE 2

A lactose monostearic acid ester was prepared in the same manner as described in Reference Example 1 but using stearyl chloride in place of arachidyl chloride.

REFERENCE EXAMPLE 3

5.3 g of 2,2',3,3',4',6,6'-hepta-O-acetyl-β-lactosylamine was dissolved in 200 ml of ethanol and 200 ml of benzene solution containing 5.62 g of arachidic acid was added to the solution 4.45 g of N-ethoxycarbonyl-2-ethoxy-1,2-dihydroquinoline was added to the mixture and the resulting mixture was stirred for 48 hours ar room temperature After cooling, the precipitate of unreacted arachidic acid was removed by filtration and the filtrate was concentrated. The residue was purified by silica gel chromatography using a mixture of chloroform and acetone (30:1) for elution to give 6.5 g of 1-N-eicosanoyl-1-deoxy-2,2',3,3',4',6,6'-hepta-O-acetyl-β-lactosylamine as a white powder.

$[\alpha]_D^{22}$ 21.5° (C=1.5 $CHCl_3$)

NMR ($CDCl_3$) δ

0.80~1.60 (39H, eicosanoyl)

1.97~2.20 (21H, all s, $COCH_3 \times 7$)

6.22 (1H, d, J=9Hz, NH)

IR(KBr)

3300 (NH)

1750 ($OCOCH_3$)

1680 (amide I)

1545 (amide II)

Analysis for $C_{46}H_{75}O_{18}N$:

Calcd: C 59.40; H 8.13; N 1.51.

Found: C 59.51; H 8.09; N 1.47.

5 g of the above product was dissolved in a mixture of 45 ml of chloroform and 130 ml of methanol mg of sodium methoxide was added to the solution, and the mixture was stirred for 4 hours at room temperature. The precipitate formed was collected by filtration and washed with methanol and ether to give 3.1 g of 1-eicosanoyl-1-deoxy-β-lactosylamine with m.p. 253~254 °C.

$[\alpha]D$ 18.63° (C=1.2 DMSO)

NMR (DMSO-$d_6$) δ

0.80~1.50 (39H, eicosanoyl)

4.60 (1H, d, J=10Hz, NH)

IR(KBr)

3400~3300 (OH,NH)

1670 (amide I)

1555 (amide II)

Analysis for $C_{32}H_{61}O_{11}N$:

Calcd: C 60.45; H. 9.67; N 2.20.

Found: C 60.22; H. 9.57; N 2.12.

EXAMPLE 1

In a mixture of chloroform and methanol were dissolved 72 μmol of egg yolk lecithin, 24 μmol of cholesterol, 8 μmol of phosphatidic acid, 4 μmol of lactose monoarachidic acid ester and 15 μCi of $^3H$-dipalmitoylphosphatidylcholine. The resulting mixture was put in a test tube, and the solvent was removed by distillation in a nitrogen gas stream. Two milliliters of a phosphate buffered saline (PBS) containing 115 μCi of $^{14}C$-tranexamic acid was added to the residue, followed by shaking to prepare a liposome suspension. The suspension was warmed at 40° C. to 45° C. and extruded through a 0.4 μm pore size of polycarbonate membrane filter to prepare liposomes with diameter less than 0.4 μm. The suspension was subjected to centrifugation 3 times at 100,000×g each for 15 minutes to remove $^{14}C$-tranexamic acid which was not encapsulated in the liposomes. PBS was added to the precipitates to make 1.6 ml of the suspension. The resulting liposome suspension was found to contain 2.3 μCi of $^3H$-dipalmitoylohosphatidylcholine and 1.8 μCi of $^{14}C$-traexamic acid both encapsulated in the liposomes per 0.5 ml of the suspension.

EXAMPLE 2

The same procedures as described in Example 1 were repeated except for using 8 μmol of lactose monoarachidic acid ester to obtain 1.8 ml of a liposome suspension. The resulting suspension was found to contain 2.3 μCi of $^3H$-dipalmitoylphosphatidylcholine and 1.8 μCi of $^{14}C$-tranexamic acid both encapsulated in the liposome per 0.5 ml of the suspension.

EXAMPLE 3

The same procedures as described in Example 1 were repeated except for using 16 μmol of lactose monoarachidic acid ester to obtain 1.8 ml of a liposome suspension. The resulting suspension was found to contain 2.3 μCi of dipalmitoylphosphatidylcholine and 1.6 μCi of $^{14}C$-tranexamic acid encapsulated in the liposomes per 0.5 ml of the suspension.

EXAMPLE 4

In a mixture of chloroform and methanol were dissolved 21.6 mg of egg yolk lecithin, 3.5 mg of cholesterol, 2.0 mg of phosphatidic acid and 3.6 mg of lactose monostearic acid ester, and the resulting solution was put in a test tube. The solvent was removed by distillation under a nitrogen gas stream, and 0.75 ml of PBS was added thereto, followed by shaking. The suspension was then warmed at 40° C. to 45° C. and, extruded through a 0.4 μm pore size of polycarbonate membrane filter to prepare liposomes with a diameter less than 0.4 μm.

TEST EXAMPLE 1

(1) A liposome suspension was prepared in the same manner as described in Example 4 but using 21.6 mg of egg yolk lecithin, 3.5 mg of cholesterol, 2.0 mg of phosphatidic acid and 0.75 ml of PBS. The suspension was applied to gel filtration chromatography [column: Sepharose CL-4B, 2.2 cmφ×42 cm; elution buffer PBS (pH 7.4); fraction size: 4 ml]. The results obtained are shown in Table 1 below.

TABLE 1

| Fraction No. | Concentration of Egg Yolk Lecithin (mg/ml) | Remark | |
|---|---|---|---|
| 10 | 0 | | |
| 11 | 0 | | |
| 12 | 0 | | |
| 13 | 0.30 | | |
| 14 | 3.22 | void volume | liposomes fraction |
| 15 | 1.68 | | |
| 16 | 0.16 | | |
| 17 | 0.05 | | |
| 18 | 0.02 | | |
| 19 | 0.02 | | |
| 20 | 0.01 | | |
| 21 | 0 | | |
| 22 | 0 | | |

TABLE 1-continued

| Fraction No. | Concentration of Egg Yolk Lecithin (mg/ml) | Remark |
|---|---|---|
| 23 | 0 | |
| 24 | 0 | |
| 25 | 0 | |
| 26 | 0 | |
| 27 | 0 | |
| 28 | 0 | |
| 29 | 0 | |
| 30 | 0 | |
| 31 | 0 | |
| 32 | 0 | |
| 33 | 0 | |
| 34 | 0 | |
| 35 | 0 | |
| 36 | 0 | |
| 37 | 0 | |
| 38 | 0 | total bed volume |
| 39 | 0 | |
| 40 | 0 | |
| 41 | 0 | |
| 42 | 0 | |
| 43 | 0 | |
| 44 | 0 | |
| 45 | 0 | |

(2) To 1.5 ml of PBS was added 5.1 mg of a lactose monoarachidic acid ester, and the solution was applied to gel filtration chromatography under the same conditions as in (1) above. The results obtained are shown in Table 2.

TABLE 2

| Fraction No. | Concentration of Lactose Monoarachidic Acid Ester (μg/ml) | Remark | Fraction No. | Concentration of Lactose Monoarachidic Acid Ester (μg/ml) | Remark |
|---|---|---|---|---|---|
| 10 | 3 | | 28 | 78 | micelle |
| 11 | 28 | | 29 | 87 | " |
| 12 | 48 | | 30 | 111 | " |
| 13 | 45 | | 31 | 63 | " |
| 14 | 26 | | 32 | 60 | " |
| 15 | 13 | | 33 | 24 | " |
| 16 | 5 | | 34 | 15 | |
| 17 | 3 | | 35 | 13 | |
| 18 | 0 | | 36 | 23 | monomer |
| 19 | 0 | | 37 | 88 | " |
| 20 | 0 | | 38 | 180 | " |
| 21 | 0 | | 39 | 129 | " |
| 22 | 0 | | 40 | 61 | " |
| 23 | 0 | | 41 | 14 | " |
| 24 | 0 | | 42 | 5 | |
| 25 | 0 | | 43 | 0 | |
| 26 | 13 | micelle | 44 | 0 | |
| 27 | 35 | " | 45 | 0 | |

(3) A liposome suspension was obtained in the same manner as described in Example 4 but using 21.6 mg of egg yolk lecithin, 3.5 mg of cholesterol, 2.0 mg of phosphatidic acid, 3.8 mg of lactose monoarachidic acid ester and 0.75 ml of PBS. The resulting suspension was applied to gel filtration chromatography under the same conditions as in (1) above. The results obtained are shown in Table 3.

TABLE 3

| Fraction No. | Concentration of Egg Yolk Lecithin (mg/ml) | Concentration of Lactose Monoarachidic Acid Ester (μg/ml) | Remark |
|---|---|---|---|
| 10 | 0 | 0 | |
| 11 | 0 | 0 | |
| 12 | 0 | 0 | |
| 13 | 0.22 | 38 | liposomes fraction |
| 14 | 2.38 | 311 | liposomes fraction |
| 15 | 2.25 | 304 | liposomes fraction |
| 16 | 0.78 | 141 | liposomes fraction |
| 17 | 0.08 | 11 | |
| 18 | 0.02 | 0 | |
| 19 | 0.01 | 0 | |
| 20 | 0.01 | 0 | |
| 21 | 0 | 0 | |
| 22 | 0 | 0 | |
| 23 | 0 | 0 | |
| 24 | 0 | 0 | |
| 25 | 0 | 0 | |
| 26 | 0 | 0 | |
| 27 | 0 | 0 | |
| 28 | 0 | 0 | |
| 29 | 0 | 0 | |
| 30 | 0 | 0 | |
| 31 | 0 | 0 | |
| 32 | 0 | 0 | |
| 33 | 0 | 0 | |
| 34 | 0 | 0 | |
| 35 | 0 | 0 | |
| 36 | 0 | 0 | |
| 37 | 0 | 20 | |
| 38 | 0 | 44 | |
| 39 | 0 | 46 | |
| 40 | 0 | 24 | |
| 41 | 0 | 4 | |
| 42 | 0 | 3 | |
| 43 | 0 | 0 | |
| 44 | 0 | 0 | |
| 45 | 0 | 0 | |

(4) An aqueous solution comprising 3.8 mg of lactose monoarachidic acid ester and 1.5 ml of PBS was added to the liposome suspension obtained in (1), and the solution was incubated at 40° C. for 1 day. The incubated solution was applied to gel filtration chromatography under the same conditions as in (1). The results obtained are shown in Table 4 below.

TABLE 4

| Fraction No. | Concentration of Egg Yolk Lecithin (mg/ml) | Concentration of Lactose Monoarachidic Acid Ester (μg/ml) | Remark |
|---|---|---|---|
| 10 | 0 | 0 | |
| 11 | 0 | 0 | |
| 12 | 0 | 0 | |
| 13 | 0.38 | 56 | liposomes fraction |
| 14 | 2.68 | 280 | liposomes fraction |
| 15 | 2.13 | 240 | liposomes fraction |
| 16 | 0.55 | 77 | liposomes fraction |
| 17 | 0.10 | 24 | liposomes fraction |
| 18 | 0 | 3 | |
| 19 | 0 | 0 | |
| 20 | 0 | 0 | |
| 21 | 0 | 0 | |
| 22 | 0 | 0 | |
| 23 | 0 | 0 | |
| 24 | 0 | 0 | |
| 25 | 0 | 0 | |
| 26 | 0 | 0 | |
| 27 | 0 | 0 | |
| 28 | 0 | 0 | |
| 29 | 0 | 0 | |
| 30 | 0 | 0 | |
| 31 | 0 | 0 | |
| 32 | 0 | 0 | |
| 33 | 0 | 0 | |
| 34 | 0 | 0 | |
| 35 | 0 | 4 | |
| 36 | 0 | 13 | |
| 37 | 0 | 31 | |
| 38 | 0 | 55 | |
| 39 | 0 | 55 | |
| 40 | 0 | 16 | |
| 41 | 0 | 2 | |
| 42 | 0 | 0 | |
| 43 | 0 | 0 | |
| 44 | 0 | 0 | |
| 45 | 0 | 0 | |

It can be seen from the results of Tables 1 to 4 that the peaks of micelle fractions of the lactose monoarachidic acid ester which are shown in Table 2 disappear in Tables 3 and 4 and that the liposome fractions of Tables 3 and 4 also show peaks of lecithin and peaks of lactose monoarachidic acid ester. This indicates that the lactose monoarachidic acid ester is incorporated into the liposomal membrane.

TEST EXAMPLE 2

(1) To 1.5 ml of PBS was added 4.8 mg of lactose monostearic acid ester, and the solution was applied to gel filtration chromatography under the same conditions as in Test Example 1-(1). The results obtained are shown in Table 5 below.

TABLE 5

| Fraction No. | Concentration of Lactose Monostearic Acid Ester (μg/ml) | Remark | Fraction No. | Concentration of Lactose Monostearic Acid Ester (μg/ml) | Remark |
|---|---|---|---|---|---|
| 10 | 0 | | 28 | 69 | micelle |
| 11 | 0 | | 29 | 94 | " |
| 12 | 0 | | 30 | 63 | " |
| 13 | 0 | | 31 | 57 | " |
| 14 | 0 | | 32 | 54 | " |
| 15 | 0 | | 33 | 31 | " |
| 16 | 0 | | 34 | 11 | |
| 17 | 0 | | 35 | 16 | |
| 18 | 0 | | 36 | 33 | monomer |
| 19 | | | 37 | 91 | " |
| 20 | 0 | | 38 | 178 | " |
| 21 | 0 | | 39 | 158 | " |
| 22 | 0 | | 40 | 101 | " |
| 23 | 0 | | 41 | 19 | " |
| 24 | 15 | | 42 | 16 | |
| 25 | 27 | | 43 | 25 | |
| 26 | 44 | micelle | 44 | 32 | |
| 27 | 57 | " | 45 | 7 | |

(2) The liposome suspension obtained in Example 4 was applied to gel filtration chromatography under the same conditions as in Test Example 1-(1). The results are shown in Table 6 below.

TABLE 6

| Fraction No. | Concentration of Egg Yolk Lecithin (mg/ml) | Concentration of Lactose Monostearic Acid Ester (μg/ml) | Remark |
|---|---|---|---|
| 10 | 0 | 0 | |
| 11 | 0 | 0 | |
| 12 | 0 | 0 | |
| 13 | 0.24 | 63 | liposomes fraction |
| 14 | 2.98 | 309 | liposomes fraction |
| 15 | 2.26 | 255 | liposomes fraction |
| 16 | 0.19 | 51 | liposomes fraction |
| 17 | 0.95 | 16 | liposomes fraction |
| 18 | 0.02 | 13 | liposomes fraction |
| 19 | 0.01 | 0 | |
| 20 | 0 | 0 | |
| 21 | 0 | 0 | |
| 22 | 0 | 0 | |
| 23 | 0 | 0 | |
| 24 | 0 | 0 | |
| 25 | 0 | 0 | |
| 26 | 0 | 0 | |
| 27 | 0 | 0 | |
| 28 | 0 | 0 | |
| 29 | 0 | 0 | |
| 30 | 0 | 0 | |
| 31 | 0 | 0 | |
| 32 | 0 | 0 | |
| 33 | 0 | 0 | |
| 34 | 0 | 0 | |
| 35 | 0 | 0 | |

TABLE 6-continued

| Fraction No. | Concentration of Egg Yolk Lecithin (mg/ml) | Concentration of Lactose Monostearic Acid Ester (μg/ml) | Remark |
|---|---|---|---|
| 36 | 0 | 7 | |
| 37 | 0 | 32 | |
| 38 | 0 | 89 | |
| 39 | 0 | 62 | |
| 40 | 0 | 12 | |
| 41 | 0 | 0 | |
| 42 | 0 | 0 | |
| 43 | 0 | 0 | |
| 44 | 0 | 0 | |
| 45 | 0 | 0 | |

It can be seen from the results of Tables 5 and 6 that the peaks of micelle fractions of the lactose monostearic acid ester which are shown in Table 5 disappear in Table 6 and that the liposome fractions of Table 6 show peaks of lecithin and peaks of lactose monostearic acid ester, indicating that the lactose monostearic acid ester is incorporated into the liposomal membrane.

TEST EXAMPLE 3

Each of the liposome suspensions obtained in Examples 1 to 3 and, as a control, a liposome suspension (total amount: 1.5 ml) prepared in the same manner as in Example 1 but using no lactose monoarachidic acid ester was intravenously injected in the hind limb vein of an SD strain male rat (body weight: 140 to 150 g) in an amount of 0.5 ml per 100 g of body weight. Thirty minutes later, the blood was drained out from the carotid artery, and the abdomen was opened to excise the liver, lung, kidney and spleen A part or the whole of each of these organs was homogenized with PBS and determine for radioactivity using a liquid scintillator to obtain a recovery (%) from each organ based on the administration dose. The radioactivity recoveries in the serum were calculated estimating the whole blood of a rat at 6.5% of the body weight and the serum at 50% of the whole blood. The results obtained are shown in Table 7. In Table 7, each value is an average of 2 animals.

The liposome suspension used as a control contained 2.3 μCi of $^3$H-dipalmitoylphosphatidylcholine (hereinafter abbreviated as $^3$H-DPPC) and 1.7 μCi of $^{14}$C-tranexamic acid encapsulated in the liposomes per 0.5 ml of the suspension.

TABLE 7

| Organ | Nucleus | Recovery (%) Control | Example 1 | Example 2 | Example 3 |
|---|---|---|---|---|---|
| liver | $^3$H-DPPC | 56.5 | 67.3 | 71.2 | 77.3 |
| | $^{14}$C-tranexamic acid | 19.0 | 24.8 | 35.0 | 50.2 |
| lung | $^3$H-DPPC | 0.38 | 0.42 | 0.32 | 0.60 |
| | $^{14}$C-tranexamic acid | 0.49 | 0.48 | 0.39 | 0.66 |
| kidney | $^3$H-DPPC | 0 | 0 | 0.08 | 0.12 |
| | $^{14}$C-tranexamic acid | 6.53 | 4.45 | 2.11 | 2.08 |
| spleen | $^3$H-DPPC | 9.53 | 7.65 | 6.22 | 4.66 |
| | $^{14}$C-tranexamic acid | 3.71 | 3.24 | 3.08 | 3.40 |
| serum | $^3$H-DPPC | 3.06 | 1.97 | 1.47 | 3.40 |
| | $^{14}$C-tranexamic acid | 2.66 | 2.16 | 2.11 | 4.27 |

It is apparent from Table 7 that distribution of the liposomes containing a lactose monoarachidic acid ester to the lung, kidney and spleen is very smaller as compared with the control that delivery to the liver can be heightened by increasing the content of the lactose monoarachidic acid ester.

TEST EXAMPLE 4

The liposome suspensions obtained in Example 2 and, as a control, a liposome suspension prepared in the same manner as in Example 1 but using no lactose monoarachidic acid ester were intravenously injected in the hind limb vein of an SD strain male rat (body weight: 140 to 150 g) in an amount of 0.5 ml per 100 g of body weight. Thirty minutes later, Nembutal was intraperitoneally injected, and the abdomen was opened. The liver was then perfused with a buffer solution for pre-perfusion and next with a collagenase solution in the manner employed by Berry-Friend and Seglen. Then, the liver was cut off using a Hanks solution for cell washing to prepare a cell suspension, which was then cooled and centrifuged to obtain a liver parenchymal cell fraction.

In the case of using the liposome suspension of Example 2, radioactivity of each of $^3$H and $^{14}$C recovered in the liver parenchymal cells was more than 85% based on that of the cell suspension, while that obtained in the case of control was about 10%.

EXAMPLE 5

In a mixture of chloroform and methanol were dissolved 68.6 μmol of L-β-dimyristoylphosphatidylcholine, 68.6 μmol of cholesterol, 6.8 μmol of dicetyl phosphate and 16 μmol of N-arachidyl-β-lactosylamine, and the resulting solution was put in a test tube. The solvent was removed by distillation in a nitrogen gas stream, and 6 ml of 1 mM inulin PBS solution containing 240 μCi of $^3$H-inulin was added thereto. After shaking, the test tube was lightly treated with ultrasonic waves to prepare a liposome suspension. The suspension was warmed at 40° C. to 45° C. and extruded through a 2 μm pore size of polycarbonate membrane filter to obtain the liposome with a diameter less than 0.2 μm. After the suspension was centrifuged twice ar 150,000×g each for 1 hour to remove inulin which was nor encapsulated in the liposomes, PBS was added thereto to make 5.62 ml of the suspension. The resulting suspension was assayed by an enzymatic method using a choline group of L-α-dimyristoylphosphatidylcholine as a marker and was found to contain 10 μmol of the total lipids per 0.5 ml of the suspension. Further, it was found that 0.64 μCi of inulin was encapsulated in the liposomes per 0.5 ml of the suspension.

EXAMPLE 6

In the same manner as described in Example 5 but using 72.4 μmol of L-α-dimyristoylphosphatidylcholine, 72.4 μmol of cholesterol, 7.2 mol of dicetyl phosphate and 8 μmol of N-arachidyl-α-lactosylamine, 5.9 ml of a liposome suspension was obtained. The resulting suspension was found to contain 10 μmol of the total lipids and 0.78 μCi of inulin encapsulated in the liposomes per 0.5 ml of the suspension.

CONTROL EXAMPLE 1

In the same manner as described in Example 5 but dissolving 76.2 μmol of L-α-dimyristoylphosphatidylcholine, 76.2 μmol of cholesterol and 7.6 μmol of dicetyl phosphate in chloroform, 5.0 ml of a liposome suspension was prepared. The resulting suspension was found to contain 10 μmol of the total lipids and 1.29 μCi of inulin encapsulated in the liposomes per 0.5 ml of the suspension.

CONTROL EXAMPLE 2

The same 1 mM inulin solution as used in Example 5 was 120-fold diluted with PBS.

TEST EXAMPLE 5

A portion of each of the liposome suspensions obtained in Example 5 and Control Example 1 was diluted with PBS so as to contain 0.5 μmol of the total lipids per one ml of the suspension.

Separately, PBS containing 100 μg/ml of lectin having sugar specificity to β-D-galactose derived from *Ricinus Communis* was prepared.

The diluted liposome suspension and the lectin solution were mixed at a volume ratio of 1:1, lightly shaken, poured into cells for spectrophotometry, and determined for percent transmission at 450 nm with the passage of time for 15 minutes. The liposome suspension of Example 5 was observed to undergo aggregation of liposomes with the passage of time, and the degree of aggregation became larger as the lectin amount increased. To the contrary, no particular aggregation occurred in the liposome suspension of Control Example 1. These results indicate that galactose residual groups are exposed on the membrane surface of the liposomes of Example 5.

TEST EXAMPLE 6

Each of the liposome suspensions obtained in Examples 5 and 6 and Control Example 1 and the $^3$H-inulin solution obtained in Control Example 2 was intravenously injected in the hind limb vein of an SD strain male rat (body weight: 140 to 160 g;) in an amount of 0.5 ml per 100 g of body weight. Thirty minutes later, the blood was drained out from the carotid artery, and the abdomen was opened to excise the liver. A part of the excised liver was homogenized with PBS. The homogenate was determined for radioactivity using a liquid scintillator to obtain a recovery (%) from the liver based on the administered dose. The radioactivity recoveries were calculated estimating the whole blood of the rat at 6.5% of the body weight and the serum at 50% of the whole blood. The results obtained are shown in Table 8.

TABLE 8

| | Recovery of Inulin, Aqueous Phase Marker | |
|---|---|---|
| | Recovery of Inulin (mean ± S.E.; %) | |
| Example No. | Liver | Serum |
| Example 5 (liposomes containing 10% of lactose monoarachidic acid amide) | 40.2 ± 0.5 (3) | 13.3 ± 4.1 (3) |
| Example 6 (liposomes containing 5% of lactose monoarachidic acid amide) | 33.4 ± 1.4 (3) | 10.8 ± 2.7 (3) |
| Control Example 1 (liposomes) | 19.4 ± 2.6 (4) | 9.9 ± 0.9 (4) |
| Control Example 2 (inulin aqueous solution) | 1.6 ± 0.2 (3) | 2.6 ± 1.1 (3) |

Note:
The parentheses indicate the number of rats.

TEST EXAMPLE 7

Inhibitory activity of asialofetuin having galactose residual groups at the terminals on delivery of the liposome suspension obtained in Example 5 or Control Example 1 to the liver was examined.

An asialofetuin solution in PBS was administered intraveneously in the hind limb vein of an SD strain male rat (body weight: 140 to 160 g) at a dose of 13.3 mg per 100 g of body weight. One minute later, the liposome suspension was intravenously injected in the hind limb vein in an amount of 0.5 ml per 100 g body weight opposite to the limb treated with asialofetuin. Thereafter, the same procedures as in Test Example 6 were repeated The results obtained are shown in Table 9.

TABLE 9

| | Inhibition by Asialofetuin on Delivery to Liver | |
|---|---|---|
| | Recovery of Inulin (means ± S.E.; %) | |
| Test Group | Example 5 | Control Example 1 |
| Non-Treated | 40.2 ± 0.5 (3) | 19.4 ± 2.6 (3) |
| Asialofetuin Treatment | 23.1 ± 3.2 (3) | 19.7 ± 2.6 (3) |

Note:
The parentheses indicate the number of rats

As is apparent from Table 9, the delivery of the liposome being incorporated a lactose monoarachidic acid amide to the liver was inhibited by administration of asialofetuin, but the inhibition of delivery was not observed in control.

While the invention has been described in detail and with reference to specific embodiments thereof, it will be apparent to one skilled in the art that various changes and modifications can be made therein without departing from the spirit and scope thereof.

What is claimed is:

1. Lipid membrane structures comprising a lactose monofatty acid ester or a lactose monofatty acid ester amide, each comprising an acyl group having from 12 to 30 carbon atoms which is substituted for a hydroxyl group of a glucose moiety of lactose in the lipid membrane thereof at a molar ratio of at least about 1:40 based on the total lipid components, wherein said lipid structures are liposomes, micelles or microemulsions, wherein the lactose monofatty acid ester and the lactose monofatty acid amide is represented by the following chemical structure:

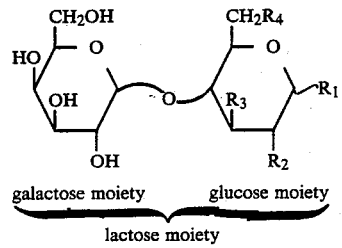

galactose moiety    glucose moiety
lactose moiety wherein one of $R_1$, $R_2$, $R_3$ and $R_4$ represents -O-acyl or -NH-acyl and the remaining three represent -OH.

2. The lipid membrane structures as claimed in claim 1, wherein said lactose monofatty acid amide is 1-N-acyl-1-deoxy-lactosylamine wherein the acyl group has from 12 to 30 carbon atoms.

3. The lipid membrane structures as claimed in claim 1, wherein the lactose monofatty acid amide is 1-N-arachidyl-1-deoxy-lactosylamine.

* * * * *